US006388111B1

(12) United States Patent
Pereira et al.

(10) Patent No.: US 6,388,111 B1
(45) Date of Patent: May 14, 2002

(54) DIALKYL QUATS

(75) Inventors: Abel G. Pereira, Belleville; Helena S. Barinova, Iselin, both of NJ (US)

(73) Assignee: Croda Inc., Parsippany, NJ (US)

( * ) Notice: Subject to any disclaimer, the term of this patent is extended or adjusted under 35 U.S.C. 154(b) by 0 days.

(21) Appl. No.: 09/409,203

(22) Filed: Sep. 30, 1999

Related U.S. Application Data

(60) Provisional application No. 60/102,779, filed on Oct. 2, 1998.
(51) Int. Cl.⁷ .............................................. C07C 233/00
(52) U.S. Cl. .............................. 554/52; 551/51; 551/56; 551/68; 551/69
(58) Field of Search .................. 510/119; 424/70.1, 424/70.6, 103; 554/52, 55, 56, 51, 68, 69

(56) References Cited

U.S. PATENT DOCUMENTS

| | | | | |
|---|---|---|---|---|
| 4,117,107 A | * | 9/1978 | Shapiro et al. ............... | 424/54 |
| 4,923,642 A | | 5/1990 | Rutzen et al. ............... | 260/404 |
| 4,954,335 A | | 9/1990 | Janchipraponvej ........... | 424/54 |
| 4,976,956 A | | 12/1990 | Noe .............................. | 424/70 |
| 5,525,245 A | | 6/1996 | Grandmaire et al. ......... | 252/8.8 |
| 5,919,958 A | * | 7/1999 | O'Lenick, Jr. ................ | 554/52 |
| 5,977,055 A | | 11/1999 | Trinh et al. .................. | 510/515 |

FOREIGN PATENT DOCUMENTS

WO    PCT/US97/18934    10/1997

* cited by examiner

*Primary Examiner*—Deborah D. Carr
(74) *Attorney, Agent, or Firm*—Lerner, David, Littenberg, Krumholz & Mentlik, LLP

(57) ABSTRACT

Dialkyl quats useful in personal care products are described. These quats are produced from fatty acids at least 30% by weight of which are C-20 in length or longer.

24 Claims, No Drawings

DIALKYL QUATS

The present invention claims the benefit of the U.S. Provisional Application No. 60/102,779 filed on Oct. 2, 1998, the disclosure of which is incorporated by reference herein.

FIELD OF THE INVENTION

The present invention relates to novel dialkyl quaternary fatty ammonium derivatives of natural and synthetic oils, fatty acids and/or triglycerides and to their use in personal care products.

BACKGROUND OF THE INVENTION

Dialkyl quaternary fatty ammonium derivatives of relatively long chain fatty acid components are known. For example, a dibehenyl dimethyl ammonium quat has been sold under the trade name INCROQUAT DBM-90 from Croda Inc., 7 Century Drive, Parsippany, N.J. 07054. Similar ammonium based quat compounds have been described in U.S. Pat. No. 4,954,335 to Ben Janchipiaponvej. However, the '335 patent describes such dialkyl quats as being selected from ammonium compounds having one or two long chain alkyl groups including from about 14 to about 22 carbon atoms. These compounds are said to be used as conditioning agents primarily for hair conditioners. It should be noted however that the '335 patent, and in addition, Noe U.S. Pat. No. 4,976,956 appear to only disclose the production of conditioning agents, not shampoos or conditioning shampoos. In addition, it has been recognized that the solubility or, more correctly, the compatibility of these compounds with anionic surfactants is limited. Indeed, in the '335 patent, even in conditioning compounds a "solubilizing" nonionic surfactant was necessary. While of course, such compounds could be used in shampoos, they can often have detrimental effects. They can reduce the foaming which is important to the action and feel of a shampoo, they add cost because of the need for an additional ingredient, present additional formulation obstacles and, in addition, add unnecessary surfactant to the shampoo, potentially increasing irritation. Dialkyl quats of compounds such as tallow are also known. However, these compounds are generally made from shorter chain fatty acid constituents, i. e. C-16 and C-18 fatty acids. Therefore, there remains a need for the production of conditioning agents which are compatible in shampoos which will not further complicate an already complicated formulation process.

SUMMARY OF THE INVENTION

The present invention relates to the dialkyl quats of fatty acid materials having at least about 30% of at least a C-20 fatty acid component by weight and preferably having a target melting point of about 100° C. or less and more preferably about 85° C. or less.

The quats in accordance with the present invention, unlike the dialkyl quats of the prior art, include an amidoamine group produced by the reaction of the carboxylic acid portion of the fatty acids with at least 2 of the nitrogens contained within a bridging molecule such as, for example, DETA.

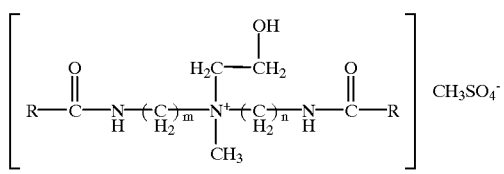

In the above formula I, R is the carbon chain of the fatty acid constituent and m and n are as described herein.

In addition, the dialkyl quats of the present invention are generally made from fatty acids having an iodine value of 200 or less, more preferably 150 or less and even more preferably 100 or less. The resulting quats can include, for example, compounds made exclusively from, for example, erucic acid (C22:1–22 carbon atoms with one double bond) or high erucic rapeseed oil ("HEAR oil"). HEAR oil has a fatty acid content of 46% by weight erucic acid (C22:1), 1.5% behemic acid (C22:0), and 11% gadoleic acid (C20:1) by weight. HEAR oil has an iodine value ranging from between about 90 to about 120 depending upon grade and actual fatty acid content. Erucic acid, by comparison, has an iodine value of about 74. Erucic acid, which makes up the major portion of HEAR oil has a target melting point of about 33.5° C.

The dialkyl quats in the present invention can also include such long chain fatty acid constituents as montan acid wax which contains, as its major constituent, a C36:0 fatty acid. Surprisingly, the compounds in accordance with the present invention have excellent anionic surfactant compatibility when compared to, for example, non-amidoamine based dialkyl quats such as those previously known. This allows them to be formulated into surfactant systems such as, for example, those present in shampoos, without the need for separate compatiblizers. Personal care products comprising a base of a shampoo, conditioner, liquid soap, facial/body wash or hair color and 0.1–10% cationic activity of the quats of the invention are also contemplated.

DETAILED DESCRIPTION OF THE PREFERRED EMBODIMENTS

Oils in accordance with the present invention include, without limitation, HEAR oil, as well as cod liver oil, herring oil, menhaden oil, mustard seed oil, pilchard oil, hear oil, salmon oil, sardine oil, meadowfoam oil and shark liver oil. The C-20+ components of some of these oils are as follows: Cod liver oil—8.8–14.6% Eicosenoic acid (C20:1), 2.6–9% Eicosapentaenoic acid (C20:5), 4.6–13.3% Docosenoic (Erucic) acid (C22:1), 1–2% Docosapentaenoic acid (C22:5) and 8.6–19% Docosahexaenoic acid (C22:6); Herring oil—1.5–19.2% Eicosenoic acid (C20:1), 4.6–10.2% Eicosapentaenoic acid (C20:5), 2.8–19.9% Docosenoic (Erucic) acid (C22:1), 1–3.7% Docosapentaenoic acid (C22:5) and 3.8–24.1% Docosahexaenoic acid (C22:6); Menhaden oil—0.9–2.7% Eicosenoic acid (C20:1), 0.6–1.2% Eicosatetraenoic acid (C20:4), 10.2–13.5% Eicosapentaenoic acid (C20:5), 0.7–1.7% Docosenoic (Erucic) acid (C22:1), 1.1–2.3% Docosapentaenoic acid (C22:5) and 3.3–14% Docosahexaenoic acid (C22:6); Pilchard (Sardine) oil—3.2% Eicosenoic acid (C20:1), 1.6% Eicosatetraenoic acid (C20:4), 16.9% Eicosapentaenoic acid (C20:5), 3.6% Docosenoic (Erucic) acid (C22:1), 2.5% Docosapentaenoic acid (C22:5) and 12.9% Docosahexaenoic acid (C22:6); HEAR oil—0.8–13.5% Eicosenoic acid (C20:1), 20.1–59.4% Docosenoic (Erucic) acid (C22:1), 0.1–1.4% Tetrcosanoic (C24:0); Mustard Seed oil—7% Eicosenoic acid (C20:1), 44.2% Docosenoic (Erucic) acid (C22:1). Oils rich in Tetracosaenoic (Nervonic) acid (C24:1) such as genetically altered HEAR oil also work well. Of course, variations in content can occur. See generally 1 "Bailey's Industrial Oil and Fat Products" (Daniel Swern, John Wiley & Sons, 4th Ed. 1979) pg. 416, 417, 447, 449, 450 and 452, all of which are attached and hereby incorporated by reference. Each of the foregoing oils has a distribution of fatty acids (usually in the form of triglcerides) which includes at least 30% of a C-20 or greater component.

Of course, it is possible in accordance with the present invention to use pure fatty acids and/or artificially created mixtures including, without limitation arachidic (C20:0) behemic (C22:0), gadoleic (C20:1), erucic (C22:1), arachadonic (C20:4) and culpodonic (C22:5). Mixtures of fatty acids are also possible which include fatty acid constituents of lower carbon chain lengths. Fatty acids may be provided from fatty acid containing oils, triglycerides and from fatty acids or salts. Indeed, fatty acid materials useful for production of dialkyl quats in accordance with the present invention can come from natural or synthetic sources and include pure fatty acids, fatty acid mixtures, triglycerides, oils, and waxes such as, for example, jojoba oil (fatty acids and fatty alcohols) or montan wax.

Reference is made herein to the use of fatty acids, or materials containing fatty acids, having a chain length of at least 20 carbon or more. If 100% euricic acid is used, then 100% of the fatty acid constituents of the quats is C-22. If HEAR oil is used, then at least 30% of the fatty acids and therefore, at least 30% of the resulting quats, will have a C-20 or higher chain length constituent. As should be clear, this means that the fatty acid component can be made up of one or more C-20 or greater fatty acids totaling at least 30% by weight of the fatty acids.

The oils or any of the pure acids contained in them should have, most preferably, but not absolutely necessary, a melt point of 100° C. or less and more preferably 85° C. or less.

The fatty acids should also be limited in terms of the degree of saturation. Preferably the majority of the fatty acid materials will either be completely saturated or mono-unsaturated. One way of measuring the degree of saturation of fatty acid is the well known iodine value used in the trade. Odor and color problems can develop as the iodine value of a fatty acid or oil containing fatty acid increases due to the products being more prone to oxidation. The odor and very dark colors obtained render the quats unacceptable for use as cosmetic ingredients. They may also render the compounds difficult to work with and compatiblize. This is particularly true when it is desired to include these ingredients in, for example, conditioning shampoos. Therefore, esters, triglycerides, acids or any combinations thereof and/or the individual fatty acids should preferably have an iodine value of 200 or less, more preferably 150 or less, and even more preferably 100 or less. Of course, if the individual fatty acid or the mixture of fatty acids has an iodine value of greater than the desired target, it may be possible to include same by hydrogenating or partially hydrogenating the material until the iodine value falls within the desired limits.

The dialkyl mono quats in accordance with the present invention can be made by taking one of the fatty acids described above such as, a triglyceride, and reacting same with a compound which can form a dialkyl amidoamine. For example, when a triglyceride is used, 2 moles of triglyceride will be reacted with 3 moles of, for example, diethylene triamine (DETA) to form 3 moles of the fatty amidoamine. The resulting secondary amidoamine can then be reacted with, for example, on alkylene oxide such as ethylene oxide to convert the secondary amine into a tertiary amine containing a alcohol group. This material can then be quaternized by a reaction with, for example (CH3)2SO4 to form the quat. Any known technique for forming quaternary amine compounds can be used. Quats so formed generally include counter ions such as halides, sulfates, phosphates and the like.

The amidoamine forming component in accordance with the present invention can be, for example, DETA as previously discussed. The amidoamine forming constituent will have the formula N1-(C)m-N2-(C)n-N3. m and n can be an integer from 1 to 6 and more preferably 1 to 4 and most preferably 1 to 3. If more than 1 carbon atom is present, the bonds between them can be saturated or unsaturated. In addition, any carbon atoms present can be substituted with, for example, one or more alkyl groups of 1 to 4 carbons, a hydroxyl containing group, an alkoxy group and the like. However, any other amidoamine forming compounds are also contemplated. For example, triethylene tetraamine (TETA), may also be used.

It should also be understood that either the nitrogen in the first, second or third position can be quaternized (amine nitrogen). The remaining 2 nitrogens would be bound to the alkyl chains (amido nitrogens). Therefore, it is possible to produce a dialkyl quat which is symmetric about the second nitrogen quat or one of the terminal nitrogens can be quaternized with the remaining 2 nitrogens bound to the alkyl groups.

In addition, the quaternized nitrogen can include a number of quaternizing groups as is known in the art. For example, as previously discussed, the quaternized nitrogen can include an ethoxy group and a methyl group as its substituents. See Formula I. Two ethoxy groups may also be used. Where it is important to render the resulting quat compatible with anionic surfactants, such as, for example, where the resulting material will be used in shampoo as opposed to a conditioner, it is important that at least one of the constituents contain, for example, a hydroxy, aldehyde, acid or other generally electro-negative group bound to the quaternized nitrogen i.e., the amine nitrogen. These can include ethoxy groups, propoxy groups, aldehydes, acids, polyethyoxy groups (polyalkoxy groups) and the like. In fact, with reference to Formula I, the ethoxy group could be replaced with a polyethyoxy group of between 2 and 20 ethoxy units. Anionic surfactant compatibility can be measured by a clear solution without precipitation or turbidity once the quat is mixed with the surfactant. Of course, if anionic surfactant compatibility is not required, then for example, two alkyl groups may be used instead, such as, for example, two methyl groups, one methyl and one ethyl group, etc.

Generally, quats in accordance with the present invention are not sold as individual compounds. Instead, they are dissolved or dispersed in a solvent or mixture of solvents. Generally, solvents can include ethylene glycol, propylene glycol, butylene glycol, dipropylene glycol, alcohol such as ethanol, isopropyl alcohol and the like. Generally, the quats in accordance with the present invention are provided in an amount of between about 25 and 90% by weight relative to the amount of solvent. More preferably between about 25 and 80% and even more preferably between 25 and 65% by weight. In addition, fatty acids or fatty alcohols can also be used resulting in a flakable material.

The formulations in accordance with the present invention are often referred to, when mixed with their solvent, as containing a certain amount of cationic activity. Therefore, a formulation including a 25% cationic activity consists of, amongst other things, 25 weight percent of a cationic quat in 75 weight percent of a solvent. Generally, the quats of the present invention are formulated in shampoos in an amount of between about 0.1 and about 10 percent based on the amount of cationic activity. Therefore, in formulating a shampoo with, for example, 1% active or 1% cationic activity, 2% of a 50/50 quat/solvent formulation by weight of the shampoo would be necessary for formulation. More preferably, the amount of activity ranges from between about 0.1% and about 5% and more preferably between about 0.5% and about 3%. On an actives basis, generally the same amounts may be used in conditioners, shampoos, colorings, liquid hand or body soaps, facial or body washes, etc.

SYNTHESIS EXAMPLE

These quats can generally be prepared in a stirred pressure vessel fitted with nitrogen, vacuum, heat and cooling, by adding 1 mole equivalent of the claimed acids and 1.5 mole equivalents of diethylenetriamine (DETA). The vessel is then heated to a temperature between 130–200° C. for 3 to 6 hours. Sample should be taken during the course of the reaction and checked via FTIR for the disappearance of the ester peak as is known to those skilled in the art. Once a negligible ester peak is obtained, the product should be cooled to a temperature between 90–130° C. and 1 or more mole equivalents of ethylene oxide added. The ethylene oxide should be allowed to react until the vessel pressure drops to its initial value. The product after the ethylene oxide addition should have a tertiary amine content of 90–100% and most preferably 95–100%. The batch should be cooled to 50–100° C. and then quaternized in the presence of propylene glycol, butylene glycol, isopropyl alcohol and the like with dimethyl sulfate, methyl chloride, benzyl chloride and the like or any other quaternizing agent generally known to those skilled in the art.

| Ingredient | % (W/W) |
|---|---|
| Shampoo | |
| ALS (30%) | 30.00 |
| Crosultaine C-50 | 3.00 |
| Crodasinic LS-30 | 4.00 |
| Dialkyl Quat | 2.00 |
| Deionized Water | 61.00 |
| Conditioner | |
| Dialkyl Quat | 3.00 |
| Oleth-10 | 1.50 |
| Crodacol S-70 | 4.00 |
| Deionized Water | 91.50 |

Note that the Dialkyl Quat is provided as 3% based on the cationic activity of the Quat/solvent mixture.

What is claimed is:

1. A dialkyl quat material comprising a quaternized dialkyl amidoamine compound derived from one or more organic substances containing fatty carboxylic acid groups, wherein said fatty carboxylic acid groups include fatty alkyl groups, said amidoamine compound having two of said fatty alkyl groups, said dialkyl quat material including at least about 30% of at least a C-20 fatty alkyl groups by weight with respect to the total weight of said fatty alkyl groups.

2. A dialkyl quat material comprising a quaternized dialkyl amidoamine compound derived from one or more organic substances containing fatty carboxylic acid groups, wherein said fatty carboxylic acid groups include fatty alkyl groups, said amidoamine compound having two of said fatty alkyl groups, wherein said substances have an iodine value of 200 or less whereby said fatty alkyl groups have a corresponding degree of unsaturation.

3. The dialkyl quat material of claim 2, wherein said organic substances have an iodine value of 150 or less.

4. The dialkyl quat material of claim 1, wherein said amidoamine compound includes three nitrogen atoms, each of said two fatty alkyl groups being connected to one of two of said nitrogen atoms via a carboxylic group whereby forming two amido groups, and the remaining nitrogen atom being the quaternary nitrogen atom.

5. A dialkyl amidoamine quat derived from one or more organic substances containing fatty carboxylic acid groups, said quat having the formula

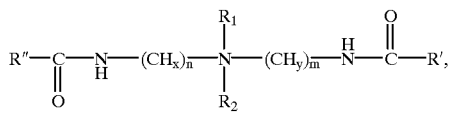

wherein R' and R" are fatty alkyl radicals of said fatty carboxylic acids groups, said fatty alkyl radicals including at least 30% of at least $C_{20}$ fatty radical by weight; y and x may range from 1 to 2; $R_1$ and $R_2$ are organic quaternizing groups, and n and m may range from 1 to 6.

6. The dialkyl quat of claim 5, wherein at least one of $R_1$ and $R_2$ is a generally electronegative group.

7. The dialkyl quat of claim 6, wherein said at least one generally electronegative group is selected from the group consisting of hydroxy, alkylhydroxy, carboxy, alkylcarboxy, aldehido, alkoxy and polyalkoxy groups.

8. The dialkyl quat of claim 6, wherein said at least one generally electro-negative group is selected from the group consisting of hydroxy, alkylhydroxy, aldehyde, acid, alkoxy and polyalkoxy groups.

9. The dialkyl quat of claim 5, wherein $R_1$ is selected from the group consisting of ethoxy, propoxy, polyalkoxy, hydroxy, and ethylhydroxy, and $R_2$ is either methyl or ethyl.

10. The dialkyl quat of claim 9, wherein $R_1$ and $R_2$ are alkyl.

11. The dialkyl quat of claim 10, wherein $R_1$ and $R_2$ are methyl or ethyl.

12. The dialkyl quat of claim 5, wherein x and y are 2, and n and m may range from 1 to 3.

13. The dialkyl quat of claim 5, wherein said each of said fatty alkyl groups R' and R" is derived from said substances having an iodine value of 200 or less.

14. The dialkyl quat of claim 5, wherein said each of said fatty alkyl groups R' and R" is derived from said substances having an iodine value of 150 or less.

15. The dialkyl quat of claim 5, wherein said each of said fatty alkyl groups R' and R" is derived from said substances having an iodine value of 100 or less.

16. The dialkyl quat of claim 5, wherein R' and R" are derived from said substances selected from the group consisting of HEAR oil, cod liver oil, herring oil, menhaden oil, mustard seed oil, pilchard oil, hear oil, salmon oil, sardine oil, meadowfoam oil and shark liver oil.

17. The dialkyl quat of claim 5, wherein R' and R" are derived from said substances selected from the group consisting of eicosenoic acid, eicosapentaenoic a, erucic acid, docosapentaenoic acid, docosahexaenoic acid, eicosatetraenoic acid, tetrcasanoic acid, arachidic acid, behemic acid, gadoleic acid, arachadonic acid and culpodonic acid.

18. The dialkyl quat of claim 5, further comprising at least one solvent.

19. The dialkyl quat of claim 1, wherein each of said two fatty alkyl groups are connected to a single bridging molecule through said carboxylic acid groups.

20. The dialkyl quat material of claim 1, 2, 3 or 4, wherein said organic substances are selected from the group consisting of HEAR oil, cod liver oil, herring oil, menhaden oil, mustard seed oil, pilchard oil, hear oil, salmon oil, sardine oil, meadowfoam oil and shark liver oil.

21. The dialkyl quat material of claim 1, 2, 3 or 4, wherein said organic substances are selected from the group consisting of eicosenoic acid, eicosapentaenoic acid, erucic acid, docosapentaenoic acid, docosahexaenoic acid, eicosatetraenoic acid, tetrcosanoic acid, arachidic acid, behemic acid, gadoleic acid, arachadonic acid and culpodonic acid.

22. The dialkyl quat material of claim 4, further comprising at least one generally electro-negative group bound to said quaternized nitrogen atom.

23. The dialkyl quat material of claim 22 wherein said at least one generally electro-negative group is selected from the group consisting of hydroxy, aldehyde, acid, alkoxy and polyalkoxy groups.

24. The dialkyl quat material of claim 1, 2, 3 or 4, further comprising at least one solvent.

* * * * *

UNITED STATES PATENT AND TRADEMARK OFFICE
CERTIFICATE OF CORRECTION

PATENT NO.     : 6,388,111 B1
DATED          : May 14, 2002
INVENTOR(S)    : Abel Pereira and Helena S. Barinova It is certified that error appears in the above-identified patent and that said Letters Patent is hereby corrected as shown below:

Column 5,
Line 64, delete "a".

Column 6,
Line 42, "9" should read -- 5 --.
Line 64, "a" should read -- acid --.

Column 7,
Line 6, "claim" should read -- claims --.
Line 11, "claim" should read -- claims --.

Column 8,
Line 11, "claim" should read -- claims --.

Signed and Sealed this

Fourth Day of February, 2003

JAMES E. ROGAN
*Director of the United States Patent and Trademark Office*